US006713650B2

(12) United States Patent
Ibrahim et al.

(10) Patent No.: US 6,713,650 B2
(45) Date of Patent: Mar. 30, 2004

(54) ABCA-1 ELEVATING COMPOUNDS

(76) Inventors: Prabha N. Ibrahim, 3380 Lubich Dr., Mountain View, CA (US) 94040; Robert Jiang, 659 Moorpark Way #1, Mountain View, CA (US) 94041; Christopher Morrison, 421 Cirrus Ave., Sunnyvale, CA (US) 94087; Kevin Shenk, 565 Arastradero Rd., Apt. 203, Palo Alto, CA (US) 94306; Jeff A. Zablocki, 580 Sleeper Ave., Mountain View, CA (US) 94040; Richard Lawn, 1927 8$^{th}$ Ave., San Francisco, CA (US) 94116

( * ) Notice: Subject to any disclaimer, the term of this patent is extended or adjusted under 35 U.S.C. 154(b) by 203 days.

(21) Appl. No.: 10/011,016

(22) Filed: Dec. 5, 2001

(65) Prior Publication Data

US 2002/0082257 A1 Jun. 27, 2002

Related U.S. Application Data

(60) Provisional application No. 60/251,916, filed on Dec. 7, 2000, and provisional application No. 60/313,274, filed on Aug. 17, 2001.

(51) Int. Cl.$^7$ ..................... C07C 233/05; A61K 31/165
(52) U.S. Cl. ..................... 564/188; 564/26; 564/90; 564/91; 564/92; 564/155; 514/585; 514/604; 514/616; 514/623
(58) Field of Search ..................... 564/26, 90, 91–92, 564/155, 188; 514/585, 604, 616, 623

(56) References Cited

U.S. PATENT DOCUMENTS

| | | |
|---|---|---|
| 3,413,285 A | 11/1968 | Tsatsas |
| 3,845,770 A | 11/1974 | Theeuwes et al. |
| 4,326,525 A | 4/1982 | Swanson et al. |
| 4,387,105 A * | 6/1983 | DeVries et al. ............ 564/49 |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,290,814 A | 3/1994 | Jackson et al. |
| 5,362,744 A * | 11/1994 | Purchase, Jr. et al. ...... 514/381 |
| 5,502,198 A | 3/1996 | Picard et al. |
| 5,616,345 A | 4/1997 | Geoghegan et al. |
| 5,760,246 A | 6/1998 | Biller et al. |

FOREIGN PATENT DOCUMENTS

| | | |
|---|---|---|
| WO | WO 99/29660 | 6/1999 |
| WO | WO 00/05201 | 2/2000 |

OTHER PUBLICATIONS

Zwarts, et al. "ABCA1 regulatory variants influence coronary artery disease independent of effects on plasma lipid levels", *Clinical Genetics*, pp. 115–125 (2002).

Yang et al., "Studies on Drugs for Coronary Heart Disease", *Acta Pharmaceutica Sinica*, pp. 18–26 (1980).

Fluka Katalog, Fluka Chemie AG, Buchs (CH), 1997, pp. 26, 27, 38, 39, 41, 46, 107, 153, 193–196, 202, 245–254, 352, 401, 414, 556, 575, 589, 594.

Chemical Abstracts, vol. 93, No. 23, 1980, "Studies on Drugs for Coronary Heart Disease".

May, et al. "Synthesis and Examination of Adamantane Derivatives as Virustatics." *Department of Virology at the Center of Hygiene*, vol. 23, No. 5, pp. 718–721 (1973) (translation enclosed).

Rupe, et al., "On the Betaines and Amino Acids of Camphor", *Helv. Chim. Acta*, vol. 17, pp. 1263–1282 (1934) (translation enclosed).

Zinner et al., "Contribution to Knowledge about UGI Reaction with Hydrazines, II", *Arch. Pharmaz*, vol. 304, pp. 933–943 (1971) (translation enclosed).

Smith et al. "Cyclic AMP Induces Apolipoprotein E Binding Activity and Promotes Cholesterol Efflux from a Macrophage Cell Line to Apolipoprotein Acceptors", *Journal of Biological Chemistry*, vol. 271, pp. 30647–30655 (1996).

Francis, et al., "Defective Removal of Cellular Cholesterol and Phospholipids by Apolipoprotein A–1 in Tangier Disease", *J. Clin. Invest.*, pp. 78–87 (1995).

Cheung, et al., "Antioxidant Supplements Block the Response of HDL to Simvastatin–Niacin Therapy in Patients with Coronary Artery Disease and Low HDL", *Arterioscler Thromb. Vas. Biol.*, pp. 1320–1326 (2001).

* cited by examiner

*Primary Examiner*—Shailendra Kumar
(74) *Attorney, Agent, or Firm*—CV Therapeutics, Inc.

(57) ABSTRACT

The present invention provides compounds that elevate cellular expression of the ABCA-1 gene, promoting cholesterol efflux from cells and increasing HDL levels in the plasma of a mammal, in particular humans. The compounds are useful for treating coronary artery disease.

64 Claims, No Drawings

ABCA-1 ELEVATING COMPOUNDS

This application claims priority to U.S. Provisional Application Serial Nos. 60/251,916 filed on Dec. 7, 2000 and 60/313,274 filed on Aug. 17, 2001.

FIELD OF THE INVENTION

The present invention relates to compounds useful for raising cellular ABCA-1 production in mammals, and to methods of using such compounds in the treatment of coronary artery diseases. The invention also relates to methods for the preparation of such compounds, and to pharmaceutical compositions containing them.

BACKGROUND OF THE INVENTION

Cholesterol is essential for the growth and viability of higher organisms. It is a lipid that modulates the fluidity of eukaryotic membranes, and is the precursor to steroid hormones such as progesterone, testosterone, and the like. Cholesterol can be obtained from the diet, or synthesized internally in the liver and the intestines. Cholesterol is transported in body fluids to specific targets by lipoproteins, which are classified according to increasing density. For example, low density lipoprotein cholesterol (LDL) is responsible for transport of cholesterol to and from the liver and to peripheral tissue cells, where LDL receptors bind LDL, and mediate its entry into the cell.

Although cholesterol is essential to many biological processes in mammals, elevated serum levels of LDL cholesterol are undesirable, in that they are known to contribute to the formation of atherosclerotic plaques in arteries throughout the body, which may lead, for example, to the development of coronary artery diseases. Conversely, elevated levels of high density lipoprotein cholesterol (HDL-C) have been found, based upon human clinical data, and animal model systems, to protect against development of coronary diseases.

In general, excess cholesterol is removed from the body by a pathway involving high density lipoproteins (HDLs). Cholesterol is "effluxed" from cells by one of two processes—either by passive transfer to mature HDL, or an active transfer to apolipoprotein A-1. The latter process is mediated by a protein known as ATP binding cassette transporter 1 (ABC-1, or alternatively referenced as ABCA-1). In the latter process, lipid-poor HDL precursors acquire phospholipid and cholesterol, which leads to increased plasma levels of mature HDL particles. HDL cholesterol is eventually transported to the liver in a process known as "reverse cholesterol transport", where it is either recycled or excreted as bile.

One method of treatment aimed at reducing the risk of formation of atherosclerotic plaques in arteries relates to decreasing plasma lipid levels. Such a method includes diet changes, and/or treatment with drugs such as derivatives of fibric acid (clofibrate, gemfibrozil, and fenofibrate), nicotinic acid, and HMG-CoA reductase inhibitors, such as mevinolin, mevastatin, pravastatin, simvastatin, fluvastatin, and lovastatin, which reduce plasma LDL cholesterol levels by either inhibiting the intracellular synthesis of cholesterol or inhibiting the uptake via LDL receptors. In addition, bile acid-binding resins, such as cholestyrine, colestipol and probucol decrease the level of LDL-cholesterol by reducing intestinal uptake and increasing the catabolism of LDL-cholesterol in the liver.

It is desired to provide alternative therapies aimed at reducing the risk of formation of atherosclerotic plaques in arteries, especially in individuals deficient in the removal of cholesterol from artery walls via the HDL pathway. Given that HDL levels are generally related to the expression of ABCA-1, one method of increasing HDL levels would be to increase the expression of ABCA-1. Accordingly, it is desired to provide compounds that are potent stimulators of the expression of ABCA-1 in mammals, thus increasing cholesterol efflux and raising HDL cholesterol levels in blood. This would be useful for the treatment of various disease states characterized by low HDL levels, in particular coronary artery disease.

It has also been shown that a combination of a drug that decreases LDL cholesterol levels and a drug that increases HDL cholesterol is beneficial; see, for example, Arterioscler., Thromn., Vasc. Biol. (2001), 21(8), 1320–1326, by Marian C. Cheung et al. Accordingly, it is also desired to provide a combination of a compound that stimulates the expression of ABCA-1 with a compound that lowers LDL cholesterol levels.

It should be noted it has also been shown that raising ABCA-1 production in macrophages locally reduces cholesterol deposition in coronary arteries without significantly raising plasma HDL cholesterol. In this instance, raising ABCA-1 expression is beneficial even in the absence of increased HDL cholesterol.

SUMMARY OF THE INVENTION

Accordingly, it is an object of this invention to provide compounds that elevate cellular expression of the ABCA-1 gene in a mammal. Accordingly, in a first aspect, the invention relates to compounds of Formula I useful for increasing ABCA-1 expression:

$$R^1-X-Y-Z-NR^2R^3 \qquad \text{Formula I}$$

wherein:
R$^1$ is optionally substituted alkyl, optionally substituted alkenyl, optionally substituted alkynyl, optionally substituted cycloalkyl, optionally substituted heterocyclyl, optionally substituted aryl, optionally substituted aralkyl, optionally substituted heteroaryl, or optionally substituted heteroaralkyl;

R$^2$ and R$^3$ are independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl; or R$^2$ and R$^3$ when taken together with the nitrogen atom to which they are attached form a heterocyclic moiety;

X is oxygen, sulfur, or —NR$^4$—;

Y is optionally substituted alkylene or a covalent bond; wherein R$^4$ is hydrogen, optionally substituted alkyl, optionally substituted cycloalkyl, —S(O)$_2$R$^5$, —C(O)R$^5$, or —C(O)NHR$^5$, in which R$^5$ is optionally substituted lower alkyl, optionally substituted cycloalkyl, optionally substituted heterocyclyl, optionally substituted aryl, or optionally substituted heteroaryl; and Z is —C(O)—Z$^1$—, —C(S)—Z$^1$—, or —SO$_2$—Z$^1$—; in which Z$^1$ is lower alkylene or a covalent bond, with the proviso that when R$^1$, R$^2$, or R$^3$ is alkenyl or alkynyl, the double bond of the alkenyl or the triple bond of the alkynyl is located at least two carbon atoms away from the attachment to the nitrogen.

In a second aspect, the invention relates to a method for using the compounds of Formula I in the treatment of a disease or condition in a mammal that can be usefully treated with a compound that elevates serum levels of HDL cholesterol, comprising administering to a mammal in need thereof a therapeutically effective dose of a compound of Formula I. Such diseases include, but are not limited to, diseases of the artery, in particular coronary artery disease.

In a third aspect, the invention relates to a method for using the compounds of Formula I in the treatment of a disease or condition in a mammal that can be usefully treated with a compound that promotes cholesterol efflux from cells, comprising administering to a mammal in need thereof a therapeutically effective dose of a compound of Formula I. Such diseases include, but are not limited to, diseases of the artery, in particular coronary artery disease.

In a fourth aspect, the invention relates to a method for using the compounds of Formula I in the treatment of a disease or condition characterized by low HDL cholesterol in a mammal that can be usefully treated with a compound that elevates serum levels of HDL cholesterol, comprising administering to a mammal in need thereof a therapeutically effective dose of a compound of Formula I. Such diseases include, but are not limited to, diseases of the artery, in particular coronary artery disease, and diabetes.

In a fifth aspect, the invention relates to a method for using the compounds of Formula I in the treatment of a condition related to coronary artery disease in a mammal that can be usefully treated with a combination of a compound that elevates serum levels of HDL cholesterol and a compound that lowers LDL cholesterol, comprising administering to a mammal in need thereof a therapeutically effective dose of a compound of Formula I and a compound that lowers LDL cholesterol.

A sixth aspect of this invention relates to pharmaceutical formulations, comprising a therapeutically effective amount of a compound of Formula I and at least one pharmaceutically acceptable excipient.

A seventh aspect of this invention relates to methods of preparing the compounds of Formula I.

Definitions and General Parameters

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH2—), ethylene (—CH2CH2—), the propylene isomers (e.g., —CH2CH2CH2— and —CH(CH3)CH2—) and the like.

The term "lower alkylene" refers to a diradical of a branched or unbranched saturated hydrocarbon chain, preferably having from 1 to 6 carbon atoms.

The term "substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF3, amino, substituted amino, cyano, or —S(O)$_n$R, in which R is alkyl, aryl, or heteroaryl and n is 0, 1 or 2; or (2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamnino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, noradamantyl, bicyclo[2.2.1]heptane, 1,3,3-trimethylbicyclo[2.2.1]hept-2-yl, (2,3,3-trimethylbicyclo[2.2.1]hept-2-yl), or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro-or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "coronary artery disease" means a chronic disease in which there is a "hardening" (atherosclerois) of the coronary arteries.

The term "atherosclerosis" refers to a form of arteriosclerosis in which deposits of yellowish plaques containing cholesterol, lipoid material, and lipophages are formed within the intima and inner media of large and medium-sized arteries.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming of the compounds of the invention is illustrated with a representative compound of Formula I in which $R^1$ is 1,3,3-trimethylbicyclo[2.2.1]hept-2-yl, $R^2$ is cyclohexyl, $R^3$ is phenyl, X is $NR^4$, in which $R^4$ is hydrogen, Y is methylene, and Z is —C(O)—.

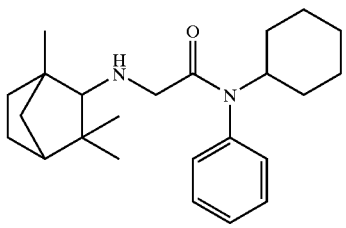

which is named: 2-(1,3,3-trimethylbicyclo[2.2.1]hept-2-ylamino)N-cyclohexyl-N-phenylacetamide.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane, DCM), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

A method for preparing the compounds of Formula I where X is —$NR^4$— and Z is —C(O)— is shown in Reaction Scheme I.

REACTION SCHEME I

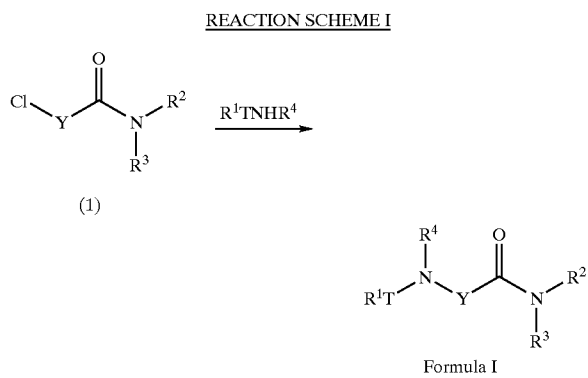

where Y is optionally substituted alkylene

Preparation of Formula I

The compound of formula (1) is either commercially available or prepared by means well known in the art. The compound of formula (1) is reacted with an amine of the formula $R^1TNHR^4$ in a protic solvent, for example isopropanol, in the presence of a tertiary base, for example triethylamine, at a temperature of between about 25° to 100° C., for about 8 to 48 hours. When the reaction is substantially complete, the product of Formula I is isolated by conventional means, for example by removal of the solvent under reduced pressure, followed by chromatography of the residue on silica gel.

An example of the preparation of a compound of formula (1) is shown below:

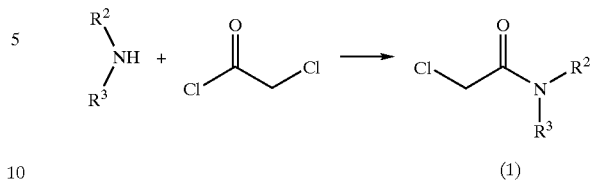

The compound of formula $R^2R^3NH$ is reacted with chloroacetyl chloride in the presence of a base, preferably sodium carbonate. The reaction is carried out in an inert solvent, preferably diethyl ether, at a temperature of about 0–30° C., for about 4–24 hours. When the reaction is substantially complete, the product of formula (1) is isolated by conventional means, for example by removal of the solvent under reduced pressure, followed by chromatography of the residue on silica gel.

Synthesis of the Compounds of Formula I

A method for preparing the compounds of Formula I where X is —$NR^4$— and Z is —$C(O)CH_2$— is shown in Reaction Scheme II.

REACTION SCHEME II

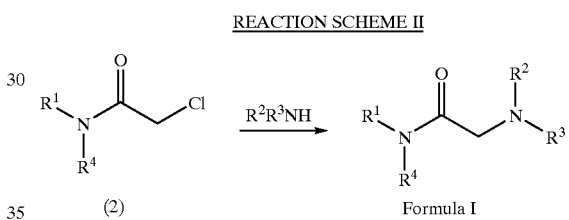

The compound of formula (2) is prepared in a manner analogous to that shown above for the compound of formula (1), by reaction of an amine of formula $R^1NR^4H$ with chloroacetyl chloride.

The compound of formula (2) is then reacted with an amine of formula $R^2R^3NH$ in the same manner as shown above in Reaction Scheme I, i.e., in a protic solvent, for example isopropanol, in the presence of a tertiary base, for example triethylamine.

Synthesis of the Compounds of Formula I

Compounds of Formula I where X is —$NR^4$—, Y is a covalent bond, and Z is —C(S)— or —$C(S)CH_2$— may be prepared by reacting the compounds of Formula I in which X is —$NR^4$—, Y is a covalent bond, and Z is —C(O)— or —$C(O)CH_2$— with Lawesson's reagent. The reaction is carried out in an inert solvent, for example chlorobenzene, at a temperature of about 80° to 120° C., for about 30 minutes to 6 hours. When the reaction is substantially complete, the product of Formula I is isolated by conventional means, for example by removal of the solvent under reduced pressure, followed by chromatography of the residue on silica gel.

Synthesis of the Compounds of Formula I

To prepare compounds of Formula I where X is —$NR^4$—, in which $R^4$ is —$C(X^1)NHR^5$, where $X^1$ is sulfur or oxygen, the compounds of Formula I in which $R^4$ is hydrogen are reacted with an isocyanate or isothiocyanate, as shown in Reaction Scheme III.

REACTION SCHEME III

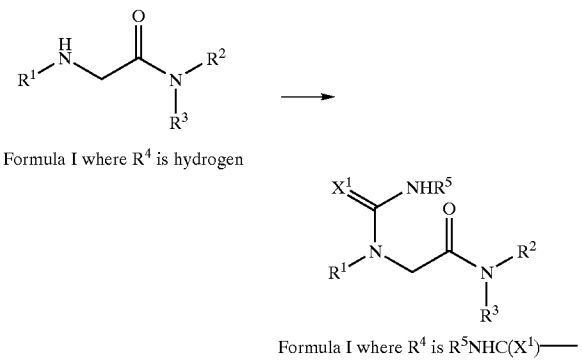

Formula I where $R^4$ is hydrogen

Formula I where $R^4$ is $R^5NHC(X^1)$—

The compound of Formula I in which $R^4$ is hydrogen is reacted with an isocyanate or isothiocyanate of formula $R^5NCX^1$, where $X^1$ is oxygen or sulfur, in the presence of a catalytic amount of 4-dimethylaminopyridine (DMAP), and a tertiary base, preferably triethylamine. The reaction is carried out in an inert solvent, for example acetonitrile, at a temperature of about 0–30° C., preferably about room temperature, for about 4–24 hours. When the reaction is substantially complete, the product of Formula I in which $R^4$ is $R^5NHC(X^1)$— is isolated by conventional means, for example by removal of the solvent under reduced pressure, followed by chromatography of the residue on silica gel.

Synthesis of the Compounds of Formula I

To prepare compounds of Formula I where X is —$NR^4$—, in which $R^4$ is —$C(X^1)R^5$, where $X^1$ is sulfur or oxygen, the compounds of Formula I in which $R^4$ is hydrogen are reacted with a compound of formula $R^5C(X^1)Cl$, as shown in Reaction Scheme IV.

REACTION SCHEME IV

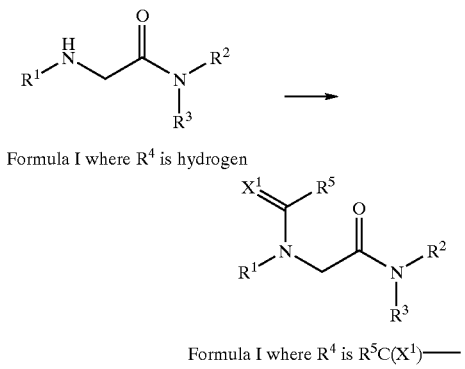

Formula I where $R^4$ is hydrogen

Formula I where $R^4$ is $R^5C(X^1)$—

The compound of Formula I in which $R^4$ is hydrogen is initially reacted with a strong base, preferably sodium hydride. The reaction is carried out in an inert solvent, preferably tetrahydrofuran, at a temperature of about 0° C., for about 1–30 minutes. After this, a compound of formula $R^5C(X^1)Cl$, where $X^1$ is oxygen or sulfur, is added, and the mixture allowed to warm to about room temperature for about 8–24 hours. When the reaction is substantially complete, the product of Formula I in which $R^4$ is $R^5C(X^1)$— is isolated by conventional means, for example by removal of the solvent under reduced pressure, followed by chromatography of the residue on silica gel.

Synthesis of the Compounds of Formula I

A method of preparing compounds of Formula I in which X is —NH—, Y is a covalent bond, and Z is —C(O)— or —C(S)— is shown in Reaction Scheme V.

REACTION SCHEME V

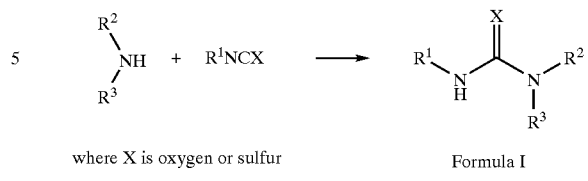

where X is oxygen or sulfur

Formula I

The amine of formula $R^2R^3NH$ is reacted with an isocyanate or isothiocyanate of formula $R^1NCX$, where X is oxygen or sulfur, in the presence of a catalytic amount of 4-dimethylaminopyridine (DMAP). The reaction is carried out in an inert solvent, for example acetonitrile, at a temperature of about 0–30° C., preferably about room temperature, for about 4–24 hours. When the reaction is substantially complete, the product of Formula I is isolated by conventional means, for example by removal of the solvent under reduced pressure, followed by chromatography of the residue on silica gel.

Synthesis of the Compounds of Formula I

A method for preparing the compounds of Formula I where X is oxygen or sulfur is shown in Reaction Scheme VI.

REACTION SCHEME VI

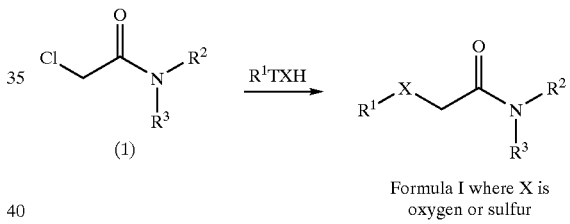

Formula I where X is oxygen or sulfur

The compound of formula $R^1XH$, where X is oxygen or sulfur (for example, a phenol or thiophenol) is reacted with the compound of formula (1) in the presence of a strong inorganic base, for example sodium hydroxide or potassium hydroxide. The reaction is carried out in an inert solvent, for example tetrahydrofuran, at a temperature of about 0–30° C., preferably about room temperature, for about 4–24 hours. When the reaction is substantially complete, the product of Formula I is isolated by conventional means, for example by removal of the solvent under reduced pressure, followed by chromatography of the residue on silica gel.

To prepare similar compounds where $R^1$ is not an aromatic group, for example where $R^1$ is alkyl or cycloalkyl, the reaction is carried out similarly, but using sodium hydride to form the anion, or where X is —NH—, the reaction is carried out in a protic solvent, preferably isopropanol, in the presence of a tertiary base, preferably triethylamine.

Synthesis of the Compounds of Formula I

A method for preparing the compounds of Formula I where X is —$NR^4$—, in which $R^4$ is —$SO_2R^5$ is shown in Reaction Scheme VII.

REACTION SCHEME VII

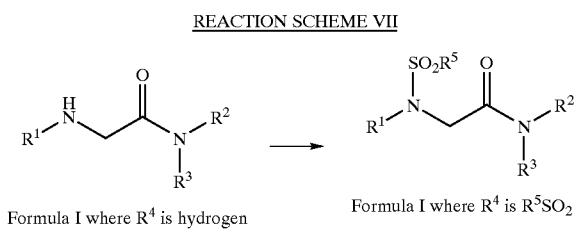

Formula I where $R^4$ is hydrogen → Formula I where $R^4$ is $R^5SO_2$

The compound of Formula I in which $R^4$ is hydrogen is reacted with a sulfonyl chloride of the formula $R^5SO_2Cl$. The reaction is carried out in an inert solvent, for example methylene chloride in the presence of a tertiary base, preferably triethylamine, at a temperature of about 0–30° C., preferably about room temperature, for about 8–24 hours. When the reaction is substantially complete, the product of Formula I in which $R^4$ is $R^5SO_2$— is isolated by conventional means, for example by removal of the solvent under reduced pressure, followed by chromatography of the residue on silica gel.

Synthesis of the Compounds of Formula I

A method for preparing the compounds of Formula I where X is —$NR^4$—, in which $R^4$ is optionally substituted alkyl is shown in Reaction Scheme VII.

REACTION SCHEME VII

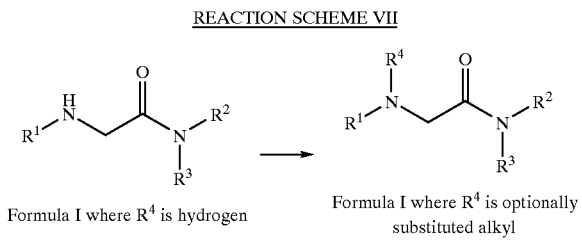

Formula I where $R^4$ is hydrogen → Formula I where $R^4$ is optionally substituted alkyl The compound of Formula I in which $R^4$ is optionally substituted alkyl is prepared from the compound of Formula I in which $R^4$ is hydrogen by a conventional reductive amination procedure. For example, reaction with formaldehyde/sodium cyanoborohydride provides a compound of Formula I in which $R^4$ is methyl. Reaction with benzaldehyde/sodium cyanoborohydride provides a compound of Formula I in which $R^4$ is benzyl (i.e., methyl substituted by phenyl). The reaction is carried out in an inert solvent, for example acetonitrile, at a pH of about 2, at a temperature of about 0–30° C., preferably about room temperature, for about 8–24 hours. When the reaction is substantially complete, the product of Formula I in which $R^4$ is optionally substituted alkyl is isolated by conventional means, for example by removal of the solvent under reduced pressure, followed by chromatography of the residue on silica gel.

Utility, Testing and Administration

General Utility

The compounds of Formula I stimulate the expression of ABCA-1 in mammalian cells, thus increasing cholesterol efflux and raising HDL levels in plasma. Therefore, the compounds of Formula I are useful for treating conditions related to high cholesterol/low HDL levels in mammals, including, but not limited to, coronary artery disease, including that produced by diabetes, and the like.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modem Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of Compounds of Formula (1) and (2)

A. Preparation of a Compound of Formula (2) in which $R^1$ is 1,3,3-trimethyl-bicyclo[2.2.1]hept-2-yl and $R^4$ is Hydrogen

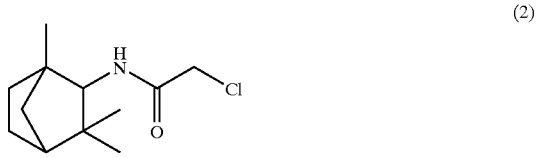

(2)

A. To a solution of 1,3,3-trimethylbicyclo[2.2.1]hept-2-ylamine (5 g, 26.3 mmol) in methylene chloride (20 ml) and triethylamine (4 ml) was added chloroacetyl chloride (2.1 ml, 26.4 mmol) dropwise. The resulting solution was stirred for 12 hours, then the solvent removed under reduced pressure. The residue was partitioned between ethyl acetate and water, the organic layer washed with brine, and dried over magnesium sulfate. The ethyl acetate solution was absorbed onto silica gel, which was eluted with 10% ethyl acetate/hexane, to yield 2-chloro-N-(1,3,3-trimethylbicyclo[2,2,1]hept-2-yl)acetamide as a white solid.

B. Preparation of a Compound of Formula (1) in which $R^1$ is Cyclohexyl and $R^2$ is Phenyl

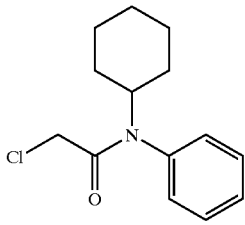

To an ice cold solution of N-cyclohexylaniline (4 mL, 0.023 mol) in diethyl ether (200 mL) mixed with aqueous saturated sodium carbonate (200 mL) chloroacetyl chloride (4 mL, 0.042 mol) was added dropwise. The mixture was allowed to warm up to room temperature and stirred for 16 hours. The organic layer was separated and the aqueous layer was extracted with diethyl ether (2×100 mL). The combined organic layer was washed with water, dried over anhydrous magnesium sulfate and evaporated to give 2-chloro-N-cyclohexyl-N-phenylacetamide as a white solid.

C. Preparation of Compounds of Formula (1) and (2) varying $R^4$

Similarly, following the procedure of 1A or 1B above, but replacing 1,3,3-trimethylbicyclo[2.2.1]hept-2-ylamine by other amines of formula $(R^1T)R^4NH$, or re[lacing N-cyclohexylaniline with other amines of formula $HNR^1R^2$, the following compounds of formula (1) and (2) are prepared:

2-chloro-N-(adamantan-1-yl)acetamide;
2-chloro-N-(bicyclo[2.2.1]heptyl)acetamide;
2-chloro-N-(1,3,3-trimethylbicyclo[2.2.1]hept-2-yl)acetamide;
2-chloro-N-((2,3,3-trimethylbicyclo[2.2.1]hept-2-yl))acetamide;
2-chloro-N-cyclohexyl-N-(4-fluorophenyl)acetamide;
2-chloro-N-cyclohexyl-N-(4-methoxyphenyl)acetamide;
2-chloro-N-cyclohexyl-N-(3,5-dichlorophenyl)acetamide;
2-chloro-N-cyclopentyl-N-phenylacetamide;
2-chloro-N-tetrahydropyran-4-yl-N-phenylacetamide;
2-chloro-N-tetrahydrofuran-3-yl-N-phenylacetamide;
2-chloro-N-piperidin-4-yl-N-phenylacetamide;
2-chloro-N-hexyl-N-phenylacetamide; and
2-chloro-N-cyclohexyl-4-yl-N-pyridin-3-ylacetamide.

EXAMPLE 2

Preparation of a Compound of Formula I

A. Preparation of a Compound of Formula I in which $R^1$ is 1,3,3-trimethyl-bicyclo[2.2.1]hept-2-yl. $R^2$ is Cyclohexyl, $R^3$ is Phenyl, X is —NH—, Y is a Covalent Bond, and Z is —C(O)CH$_2$—

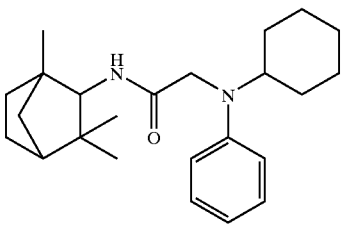

Formula I

To a solution of N-cyclohexylaniline (100 mg, 0.56 mmol) in tetrahydrofuran (4 ml) at −78° C. was added LiHMDS (1 ml of a 1M solution in tetrahydrofuran) dropwise. The solution was allowed to warm to 0° C., then recooled to −78° C., and a solution of 2-chloro-N-(1,3,3-trimethylbicyclo[2,2,1]hept-2-yl)acetamide (124 mg, 0.56 mmol) in tetrahydrofuran (1 ml) added dropwise. The mixture was allowed to warm to room temperature, and was stirred for 1 hour. Water was added, and the mixture was extracted with ethyl acetate. The organic layer was washed with brine, and dried over magnesium sulfate. The ethyl acetate solution was absorbed onto silica gel, which was eluted with 3% methanol/methylene chloride, to yield 2-(cyclohexylphenylamino)-N-(1,3,3-trimethylbicyclo[2.2.1]hept-2-yl)acetamide.

B. Preparation of a Compound of Formula I in which X is —NH—, Y is a Covalent Bond, varying $R^1$, $R^2$, $R^3$, and Z Similarly, following the procedure of 2A above, but replacing LiHMDS/tetrahydrofuran by triethylamine/isopropanol, and optionally replacing N-cyclohexylaniline by other amines of formula $R^1NH_2$ or $R^2R^3NH$, and optionally replacing 2-chloro-N-(1,3,3-trimethylbicyclo[2,2,1]hept-2-yl)acetamide by other compounds of formula (1) or (2), the following compounds of Formula I were prepared:

2-(1-methyladamantan-2-ylamino))-N-cyclohexyl-N-phenylacetamide;
2-(noradamantan-3-ylamino))-N-cyclohexyl-N-phenylacetamide;
2-[(7,7-dimethylbicyclo[2.2.1]hept-2-yl)amino]-N-cyclohexyl-N-phenylacetamide;
2-[(5S,2R)-5-methyl-2-isopropylcyclohexylamino]-N-cyclohexyl-N-phenylacetamide;
2-[(1R,2R)-2-methylcyclohexylamino]-N-cyclohexyl-N-phenylacetamide;
2-[((1 S,3 S,4S)-3,5,5-trimethylbicyclo[2.2.1]hept-2-yl)amino]-N-cyclohexyl-N-phenylacetamide;
2-[2-(phenylethyl)amino]-N-cyclohexyl-N-phenylacetamide;
2-(cyclohexylamino)-N-cyclohexyl-N-phenylacetamide;
2-(cyclopentylamino)-N-cyclohexyl-N-phenylacetamide;
2-(benzylamino)-N-cyclohexyl-N-phenylacetamide;
2-[(1,3,3-trimethylbicyclo[2.2.1]hept-2-yl)amino]-N-cyclohexyl-N-phenylacetamide;
2-[(1,2,2-trimethylpropyl)amino]-N-cyclohexyl-N-phenylacetamide;
2-(cyclohexylphenylamino)-N-(adamantan-1-yl)acetamide;
2-(cyclohexylphenylamino)-N-(bicyclo[2.2.1]heptyl)acetamide; and
2-(cyclohexylphenylamino)-N-(2,3,3-trimethylbicyclo[2.2.1]hept-2-yl)acetamide.

C. Preparation of a Compound of Formula I in which X is —NH—, Y is a Covalent Bond, varying $R^1$, $R^2$, $R^3$, and Z Similarly, following the procedure of 2A above, but optionally replacing N-cyclohexylaniline by other amines of formula $R^1NH_2$ or $R^2R^3NH$, and optionally replacing 2-chloro-N-(1,3,3-trimethylbicyclo[2,2,1 ]hept-2-yl)

acetamide by other compounds of formula (1) or (2), the following compounds of Formula I are prepared:
2-[3,5,5-trimethylbicyclo[2.2.1]hept-2-yl)amino]-N-cyclohexyl-N-(4-fluorophenyl)acetamide;
2-[3,5,5-trimethylbicyclo[2.2.1]hept-2-yl)amino]-N-cyclohexyl-N-(4-methoxyphenyl)acetamide;
2-[3,5,5-trimethylbicyclo[2.2.1]hept-2-yl)amino]-N-cyclohexyl-N-(3,5-dichlorophenyl)acetamide;
2-[3,5,5-trimethylbicyclo[2.2.1]hept-2-yl)amino]-N-cyclopentyl-N-phenylacetamide;
2-[3,5,5-trimethylbicyclo[2.2.1]hept-2-yl)amino]-N-(tetrahydropyran-4-yl)-N-(4-fluorophenyl)acetamide;
2-[3,5,5-trimethylbicyclo[2.2.1]hept-2-yl)amino]-N-(tetrahydrofuran-3-yl)-N-(4-fluorophenyl)acetamide;
2-[3,5,5-trimethylbicyclo[2.2.1]hept-2-yl)amino]-N-(piperidin-4-yl)-N-phenylacetamide;
2-[3,5,5-trimethylbicyclo[2.2.1]hept-2-yl)amino]-N-hexyl-N-phenylacetamide; and
2-[3,5,5-trimethylbicyclo[2.2.1]hept-2-yl)amino]-N-cyclohexyl-N-(pyridin-3-yl)acetamide.

EXAMPLE 3

Preparation of a Compound of Formula I
A. Preparation of a Compound of Formula I in which $R^1$ is 1,3,3-trimethyl-bicyclo[2.2.1]hept-2-yl, $R^2$ is Cyclohexyl, $R^3$ is Phenyl, $R^4$ is —C(O)$R^5$, $R^5$ is 2-Fluorophenyl, X is —NH—, Y is a Covalent Bond, and Z is —C(O)—

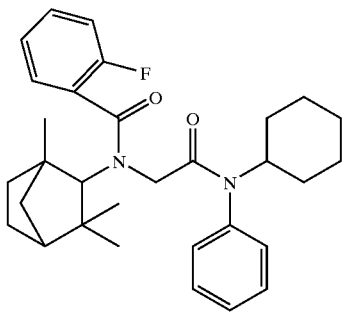

To a cooled solution of 2-[(1,3,3-trimethylbicyclo[2.2.1] hept-2-yl)amino]-N-cyclohexyl-N-phenylacetamide (50 mg, 0.124 mmol, as its hydrochloride salt) in anhydrous tetrahydrofuran sodium hydride in mineral oil (11 mg, 0.275 mmol) was added, and the mixture stirred at 0° C. for 10 minutes under nitrogen. To this mixture a solution of 2-fluorobenzoyl chloride (30 µl, 0.246 mmol) in tetrahydrofuran (1 ml) was added slowly. The mixture was allowed to warm to room temperature, and was then stirred overnight. Concentration of the reaction product under reduced pressure afforded a yellow oil, which was quenched with saturated ammonium chloride and extracted with ethyl acetate. The organic layer was washed with saturated sodium bicarbonate solution, followed by brine, and dried over anhydrous magnesium sulfate. The solvent was removed under reduced pressure, and the residue purified using preparative silica gel plates with 10% ethyl acetate/hexanes as the solvent, affording 2-[(2-fluorophenyl)-N-(1,3,3-trimethylbicyclo[2.2.1]hept-2-yl}carbonylamino]-N-cyclohexyl-N-phenylacetamide.
B. Preparation of a Compound of Formula I in which $R^1$ is 1,3,3-trimethyl-bicyclo[2.2.1]hept-2-yl, $R^2$ is Cyclohexyl, $R^3$ is Phenyl, X is —NH—, Y is a Covalent Bond, and Z is —C(O)—, varying $R^4$ Similarly, following the procedure of 3A above, but replacing 2-fluorobenzoyl chloride by other compounds of formula $R^5C(X^1)Cl$, the following compounds of Formula I were prepared:
2-[trifluoromethyl-N-(1,3,3-trimethylbicyclo[2.2.1]hept-2-yl]carbonylamino]-N-cyclohexyl-N-phenylacetamide;
2-[phenyl-N-(1,3,3-trimethylbicyclo[2.2.1]hept-2-yl}carbonylamino]-N-cyclohexyl-N-phenylacetamide;
2-[N-(1,3,3-trimethylbicyclo[2.2.1]hept-2-yl}acetylamino]-N-cyclohexyl-N-phenylacetamide; and
2-{[4-methoxyphenyl]-N-1,3,3-trimethylbicyclo[2.2.1] hept-2-yl}carbonylamino]-N-cyclohexyl-N-phenylacetamide.
C. Preparation of a Compound of Formula I varying $R^1$, $R^2$, $R^3$, $R^4$, X, —NH—, Y, and Z Similarly, following the procedure of 3A above, but optionally replacing 2-fluorobenzoyl chloride by other compounds of formula $R^5C(X^1)Cl$, and optionally replacing 2-[(1,3,3-trimethylbicyclo[2.2.1]hept-2-yl)amino]-N-cyclohexyl-N-phenylacetamide by other compounds of Formula I in which $R^4$ is hydrogen, other compounds of Formula I are prepared.

EXAMPLE 4

Preparation of a Compound of Formula I
A. Preparation of a Compound of Formula I in which $R^1$ is Benzyl, $R^2$ is Cyclohexyl, $R^3$ is Phenyl, $R^4$ is Hydrogen, X is —NH—, Y is a Covalent Bond, and Z is —C(S)—

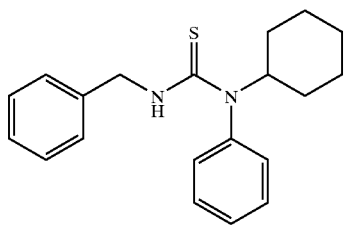

To a solution of N-cyclohexylaniline (0.1 ml, 0.57 mmol) in acetonitrile (4 ml) was added a catalytic amount of 4-(dimethylamino)pyridine (5 mg, 0.04 mmol). To this mixture was added benzyl isothiocyanate (0.11 ml, 0.83 mmol) dropwise, and the mixture was stirred at room temperature for 16 hours. The solvent was removed under reduced pressure, and the residue purified on preparative silica gel plates, developing with 20% ethyl acetate/hexanes, to furnish (cyclohexylphenylamino)-N-benzylthiocarboxamide as a white solid, (M+1)=324.8.
B. Preparation of a Compound of Formula I in which $R^1$ is Benzyl, $R^2$ is Cyclohexyl, $R^4$ is Hydrogen, X is —NH—, Y is a Covalent Bond, and Z is —C(O) or —C(S)—, varying $R^3$, Similarly, following the procedure of 4A above, but replacing benzyl isothiocyanate by other compounds of formula $R^1TNCX$, where X is oxygen or sulfur, the following compounds of Formula I were prepared:
(cyclohexylphenylamino)-N-benzylcarboxamide;
(cyclohexylphenylamino)-N-(2-fluorophenyl) thiocarboxamide;
(cyclohexylphenylamino)-N-phenylthiocarboxamide;
(cyclohexylphenylamino)-N-phenylcarboxamide;
(cyclohexylphenylamino)-N-(bicyclo[2.2.1]hept-2-yl) thiocarboxamide;)
(cyclohexylphenylamino)-N-(2,3,3-trimethylbicyclo[2.2.1] hept-2-yl)thiocarboxamide;
C. Preparation of a Compound of Formula I, varying $R^1$, $R^2$, $R^3$, $R^4$, X, —NH—, T, Y, and Z Similarly, following the procedure of 4A above, but optionally replacing N-cyclohexylaniline by other compounds of formula R²R³NH, and optionally replacing benzyl isothiocyanate by other compounds of formula R¹TNCX, where X is oxygen or sulfur, other compounds of Formula I are prepared.

EXAMPLE 5
Preparation of a Compound of Formula I

A. Preparation of a Compound of Formula I in which $R^1$ is 1,3,3-trimethyl-bicyclo[2.2.1]hept-2-yl, $R^2$ is Cyclohexyl, $R^3$ is Phenyl, $R^4$ is Methylaminocarbonyl, X is —$NR^4$—, Y is Methylene, and Z is —C(O)—

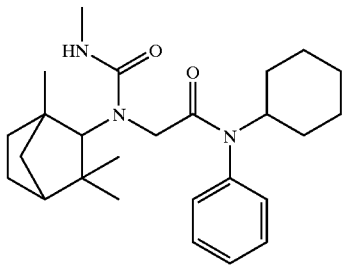

To a solution of 2-[(1,3,3-trimethylbicyclo[2.2.1]hept-2-yl)amino]-N-cyclohexyl-N-phenylacetamide as its hydrochloride salt (93 mg, 0.23 mmol) in acetonitrile (5 ml) was added triethylamine (0.04 ml, 0.29 mmol) and a catalytic amount of 4-(dimethylamino)pyridine (5 mg, 0.04 mmol). Methyl isocyanate (500 mg, 8.8 mmol) was added dropwise, and the solution was stirred at room temperature for 16 hours. The solvent was removed under reduced pressure, and the residue purified on preparatory plates using 10% ethyl acetate/hexanes, to furnish 2-[(methylamino)-N-(1,3,3-trimethylbicyclo[2.2.1]hept-2-yl)carbonylamino]-N-cyclohexyl-N-phenylacetamide;

B. Preparation of a Compound of Formula I in which $R^1$ is 1,3,3-trimethyl-bicyclo[2.2.1]hept-2-yl, $R^2$ is Cyclohexyl, $R^3$ is Phenyl, $R^4$ is Methylaminocarbonyl, X is —$NR^4$—, Y is Methylene, and Z is —C(S)—

Similarly, following the procedure of 5A above, replacing methyl isocyanate by methyl isothiocyanate, 2-[(methylamino)-N-(1,3,3-trimethylbicyclo[2.2.1]hept-2-yl)thiocarbonylamino]-N-cyclohexyl-N-phenylacetamide was prepared.

C. Preparation of a Compound of Formula I in which $R^4$ is X is —O— or —S—, varying $R^1$, $R^2$, $R^3$, $R^4$, X, —NH—, Y, and Z Similarly, following the procedure of 5A above, but optionally replacing 2-[(1,3,3-trimethylbicyclo[2.2.1]hept-2-yl)amino]-N-cyclohexyl-N-phenylacetamide by other compounds of Formula I in which $R^4$ is hydrogen, and optionally replacing methyl isocyanate by other compounds of formula $R^5NCX^1$, where $X^1$ is oxygen or sulfur, the following compounds of Formula I are prepared:

2-[(methylamino)-N-(1-methyladamantan-2-yl) carbonylamino]-N-cyclohexyl-N-phenylacetamide;
2-[(methylamino)-N-((5S,2R)-5-methyl-2-isopropylcyclohexyl)carbonylamino]-N-cyclohexyl-N-phenylacetamide;
2-[(methylamino)-N-(2-methylcyclohexyl)carbonylamino]-N-cyclohexyl-N-phenylacetamide;
2-[(methylamino)-N-(3,5,5-trimethylbicyclo[2.2.1]hept-2-yl))carbonylamino]-N-cyclohexyl-N-phenylacetamide;
2-[(methylamino)-N-(2-phenylethyl)carbonylamino]-N-cyclohexyl-N-phenylacetamide;
2-[(methylamino)-N-(cyclohexyl)carbonylamino]-N-cyclohexyl-N-phenylacetamide;
2-[(methylamino)-N-(cyclopentyl)carbonylamino]-N-cyclohexyl-N-phenylacetamide;
2-[(methylamino)-N-(1,2,2-trimethylpropyl) carbonylamino]-N-cyclohexyl-N-phenylacetamide;
2-[(methylamino)-N-(1-methyladamantan-2-yl) thiocarbonylamino]-N-cyclohexyl-N-phenylacetamide;
2-[(methylamino)-N-((5S,2R)-5-methyl-2-isopropylcyclohexyl)thiocarbonylamino]-N-cyclohexyl-N-phenylacetamide;
2-[(methylamino)-N-(2-methylcyclohexyl) thiocarbonylamino]-N-cyclohexyl-N-phenylacetamide;
2-[(methylamino)-N-(3,5,5-trimethylbicyclo[2.2.1]hept-2-yl))thiocarbonylamino]-N-cyclohexyl-N-phenylacetamide;
2-[(methylamino)-N-(2-phenylethyl)thiocarbonylamino]-N-cyclohexyl-N-phenylacetamide;
2-[(methylamino)-N-(cyclohexyl)thiocarbonylamino]-N-cyclohexyl-N-phenylacetamide;
2-[(methylamino)-N-(cyclopentyl)thiocarbonylamino]-N-cyclohexyl-N-phenylacetamide; and
2-[(methylamino)-N-(1,2,2-trimethylpropyl) thiocarbonylamino]-N-cyclohexyl-N-phenylacetamide.

EXAMPLE 6
Preparation of a Compound of Formula I

A. Preparation of a Compound of Formula I in which $R^1$ is 4-Fluorophenyl, $R^2$ is Cyclohexyl, $R^3$ is Phenyl, $R^4$ is Methylaminocarbonyl, X is —S—, Y is Methylene, and Z is —C(O)—

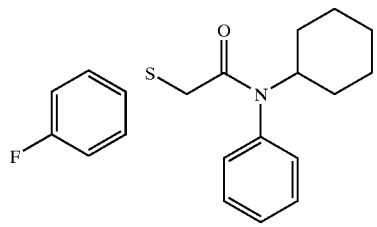

To a stirred solution of 4-fluorothiophenol (0.13 mL, 1.2 mmol) in tetrahydrofuran (4 ml) was added aqueous 15% sodium hydroxide. 2-Chloro-N-cyclohexyl-N-phenylacetamide (320 mg, 1.3 mmol) was added, and the solution was stirred at room temperature for 16 hours. The solvent was removed under reduced pressure, and the residue purified on a preparatory plate using 20% ethyl acetate/hexanes to furnish 2-(4-fluorophenylthio)-N-cyclohexyl-N-phenylacetamide as a white solid. (M+1)=343.9

B. Preparation of a Compound of Formula I in which $R^1$ is 4-Fluorophenyl, $R^2$ is Cyclohexyl, $R^3$ is Phenyl, $R^4$ is Methylaminocarbonyl, X is —O—, Y is Methylene, and Z is —C(O)—

Similarly, following the procedure of 6A above, but replacing fluorothiophenol by phenol, 2-phenoxy-N-cyclohexyl-N-phenylacetamide was prepared.

C. Preparation of a Compound of Formula I in which X is —O— or —S—, varying $R^1$, $R^2$, $R^3$, $R^4$, —NH—, Y, and Z Similarly, following the procedure of 6A above, but replacing fluorothiophenol by other compounds of formula $R^1TXH$, the following compounds of Formula I are prepared:

2-(phenylthio)-N-cyclohexyl-N-phenylacetamide;
2-(4-methoxyphenylthio)-N-cyclohexyl-N-phenylacetamide;
2-(4-trifluoromethylphenylthio)-N-cyclohexyl-N-phenylacetamide;

2-(4-fluorophenylthio)-N-cyclohexyl-N-phenylacetamide;
2-(3,5-dichlorophenylthio)-N-cyclohexyl-N-phenylacetamide;
2-(phenoxy)-N-cyclohexyl-N-phenylacetamide;
2-(4-methoxyphenoxy)-N-cyclohexyl-N-phenylacetamide;
2-(4-trifluoromethylphenoxy)-N-cyclohexyl-N-phenylacetamide;
2-(4-fluorophenoxy)-N-cyclohexyl-N-phenylacetamide; and
2-(3,5-dichlorophenoxy)-N-cyclohexyl-N-phenylacetamide.

EXAMPLE 7

Preparation of a Compound of Formula I

A. Preparation of a Compound of Formula I in which $R^1$ is 1,3,3-trimethyl-bicyclo[2.2.1]hept-2-yl, $R^2$ is Cyclohexyl, $R^3$ is Phenyl. $R^4$ is Toluenesulfonyl, X is —N—, Y is Methylene, and Z is —C(O)—

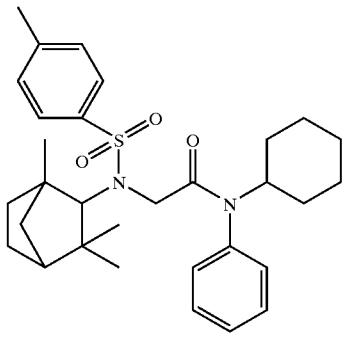

To a solution of 2-[(1,3,3-trimethylbicyclo[2.2.1]hept-2-yl)amino]-N-cyclohexyl-N-phenylacetamide (30 mg, 0.07 mmol) in methylene chloride (5 ml) was added p-toluenesulfonyl chloride (14 mg, 0.07 mmol). The resulting solution was stirred at room temperature for 18 hours. The solvent was removed under reduced pressure, and the residue partitioned between ethyl acetate and water. The organic layer was washed with water, then brine, and dried over magnesium sulfate. The resulting solution was purified by absorbing the solution on silica gel and eluting with 20% ethyl acetate/hexanes. on preparatory plates using 10% ethyl acetate/hexanes, to furnish 2-{[(4-methylphenyl)sulfonyl](1,3,3-trimethylbicyclo[2.2.1]hept-2-yl)carbonylamino}-N-cyclohexyl-N-phenylacetamide;

B. Preparation of a Compound of Formula I in which $R^1$ is 1,3,3-trimethyl-bicyclo[2.2.1]hept-2-yl $R^2$ is Cyclohexyl $R^3$ is Phenyl $R^4$ is Phenylsulfonyl X is —N— Y is Methylene, and Z is —C(O)—

Similarly, following the procedure of 7A above, replacing p-toluenesulfonyl chloride by phenylsulfonyl chloride, 2-[(phenylsulfonyl)(1,3,3-trimethylbicyclo[2.2.1]hept-2-yl)carbonylamino]-N-cyclohexyl-N-phenylacetamide; was prepared.

C. Preparation of a Compound of Formula I in which X is —N— and $R^4$ is —$SO_2R^5$, varying $R^1$, $R^2$, $R^3$, $R^5$, T, Y, and Z Similarly, following the procedure of 7A above, but optionally replacing p-toluenesulfonyl chloride by other compounds of formula $R^5SO_2Cl$, and optionally replacing 2-[(1,3,3-trimethylbicyclo[2.2.1]hept-2-yl)amino]-N-cyclohexyl-N-phenylacetamide by other compounds of Formula I in which $R^4$ is hydrogen, other compounds of Formula I are prepared.

EXAMPLE 8

Preparation of a Compound of Formula I

A. Preparation of a Compound of Formula I in which $R^1$ is 1,3,3-trimethyl-bicyclo[2.2.1]hept-2-yl, $R^2$ is Cyclohexyl, $R^3$ is Phenyl, X is —NH—, Y is Methylene, and Z is —C(S)—

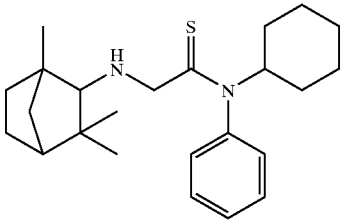

To a stirred solution of 2-[(1,3,3-trimethylbicyclo[2.2.1]hept-2-yl)amino]-N-cyclohexyl-N-phenylacetamide (110 mg, 0.272 mmol) in chlorobenzene (3 mL) was added Lawesson's reagent (70 mg, 0.17 mmol). The solution was stirred at 120° C. for 2 hours. The solvent was removed under reduced pressure, and the residue purified on preparatory plate using 15% ethyl acetate/hexanes to furnish 2-[(1,3,3-trimethylbicyclo[2.2.1]hept-2-yl)amino]-N-cyclohexyl-N-phenylthioacetamide as a yellow solid. (M+1)=385.0]

B. Preparation of a Compound of Formula I in which Z is —C(S)—

Similarly, following the procedure of 8A above, but replacing 2-[(1,3,3-trimethylbicyclo[2.2.1]hept-2-yl)amino]-N-cyclohexyl-N-phenylacetamide by other compounds of Formula I in which Z is —C(O)—, the following compounds of Formula I are prepared:

2-(1-methyladamantan-2-ylamino))-N-cyclohexyl-N-phenylthioacetamide;
2-[(5S,2R)-5-methyl-2-isopropylcyclohexylamino]-N-cyclohexyl-N-phenylthioacetamide;
2-[(1R,2R)-2-methylcyclohexylamino]-N-cyclohexyl-N-phenylthioacetamide; 2-[((1S,3S,4S)-3,5,5-trimethylbicyclo[2.2.1]hept-2-yl)amino]-N-cyclohexyl-N-phenylthioacetamide;
2-[2-(phenylethyl)amino]-N-cyclohexyl-N-phenylthioacetamide;
2-(cyclohexylamino)-N-cyclohexyl-N-phenylthioacetamide;
2-(cyclopentylamino)-N-cyclohexyl-N-phenylthioacetamide;
2-(benzylamino)-N-cyclohexyl-N-phenylthioacetamide;
2-[(1,3,3-trimethylbicyclo[2.2.1]hept-2-yl)amino]-N-cyclohexyl-N-phenylthioacetamide;
2-[(1,2,2-trimethylpropyl)amino]-N-cyclohexyl-N-phenylthioacetamide;
2-(cyclohexylphenylamino)-N-(adamantan-1-yl)thioacetamide;
2-(cyclohexylphenylamino)-N-(bicyclo[2.2.1]heptyl)thioacetamide;
2-(cyclohexylphenylamino)-N-(2,3,3-trimethylbicyclo[2.2.1]hept-2-yl)thioacetamide;
2-[3,5,5-trimethylbicyclo[2.2.1]hept-2-yl)amino]-N-cyclohexyl-N-(4-fluorophenyl)thioacetamide;
2-[3,5,5-trimethylbicyclo[2.2.1]hept-2-yl)amino]-N-cyclohexyl-N-(4-methoxyphenyl)thioacetamide;
2-[3,5,5-trimethylbicyclo[2.2.1]hept-2-yl)amino]-N-cyclohexyl-N-(3,5-dichlorophenyl)thioacetamide;
2-[3,5,5-trimethylbicyclo[2.2.1]hept-2-yl)amino]-N-cyclopentyl-N-phenylthioacetamide;
2-[3,5,5-trimethylbicyclo[2.2.1]hept-2-yl)amino]-N-(tetrahydropyran-4-yl)-N-(4-fluorophenyl)thioacetamide;
2-[3,5,5-trimethylbicyclo[2.2.1]hept-2-yl)amino]-N-(tetrahydrofuran-3-yl)-N-(4-fluorophenyl)thioacetamide;

2-[3,5,5-trimethylbicyclo[2.2.1]hept-2-yl)amino]-N-(piperidin-4-yl)-N-phenylthioacetamide;
2-[3,5,5-trimethylbicyclo[2.2.1]hept-2-yl)amino]-N-hexyl-N-phenylthioacetamide; and
2-[3,5,5-trimethylbicyclo[2.2.1]hept-2-yl)amino]-N-cyclohexyl-N-(pyridin-3-yl)thioacetamide.

EXAMPLE 9

Preparation of a Compound of Formula I

A. Preparation of a Compound of Formula I in which $R^1$ is 1,3,3-trimethyl-bicyclo[2.2.1]hept-2-yl, $R^2$ is Cyclohexyl. $R^3$ is Phenyl, $R^4$ is Methyl, X is —N—, Y is Methylene, and Z is —C(O)—

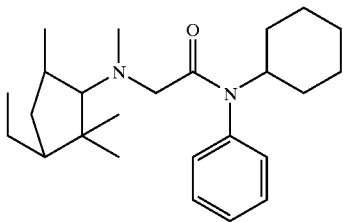

A. To a solution of 2-[(1,3,3-trimethylbicyclo[2.2.1]hept-2-yl)amino]-N-cyclohexyl-N-phenylacetamide (50 mg, 0.124 mmol) in acetonitrile (1 mL) was added formaldehyde (40% aqueous solution; 0.150 mL) followed by the addition of sodium cyanoborohydride (20 mg). The pH of the solution was adjusted to 2 by the addition of aq. HCl and the reaction mixture was stirred for 16 hours. The solvent was evaporated and product purified by preparative TLC using ethyl acetate as the solvent, to provide 2-[(1,3,3-trimethylbicyclo[2.2.1]hept-2-yl)methylamino]-N-cyclohexyl-N-phenylacetamide. M+1=383.0

B. Preparation of a Compound of Formula I in which $R^1$ is 1,3,3-trimethyl-bicyclo[2.2.1]hept-2-yl, $R^2$ is Cyclohexyl $R^3$ is Phenyl $R^4$ is Benzyl, X is —N—, Y is Methylene, and Z is —C(O)—

Similarly, following the procedure of 9A above, replacing formaldehyde by benzaldehyde, 2-[(1,3,3-trimethylbicyclo[2.2.1]hept-2-yl)benzylamino]-N-cyclohexyl-N-phenylacetamide was prepared.

C. Preparation of a Compound of Formula I in which $R^4$ is Optionally Substituted Alkyl, and Z is —C(S)—

Similarly, following the procedure of 9A above, but replacing 2-[(1,3,3-trimethylbicyclo[2.2.1]hept-2-yl)amino]-N-cyclohexyl-N-phenylacetamide by other compounds of Formula I in which Z is —C(O)—, other compounds of Formula I are prepared.

EXAMPLE 10 pGL3 Luciferase Assay

This example shows the effect of the compounds of the invention on ABCA-1 gene expression, using the pGL3 luciferase reporter vector system (Promega, Madison, Wis.) to create a recombinant plasmid to measure reporter gene expression under control of the ABCA-1 promoter.

Construction of Reporter Plasmids

Plasmid pGL3-Basic (Promega, Madison, Wis.; Cat. #E1751) was used as a control plasmid containing the promoterless luciferase gene. The reporter construct containing the ABCA-1 promoter and luciferase gene was made by cloning a genomic fragment from the 5' flanking region of the ABCA-1 gene (hAPR1 5' promoter, corresponding to nucleotides 1080–1643 of SEQ ID NO: 3) into the SacI site of the GL3-Basic plasmid to generate plasmid GL-6a. Next, plasmid GL-6a was digested with SpeI and Acc65I. A BsiWI-SpeI fragment excised from a lambda subclone, representing the ABCA-1 genomic sequence corresponding to nucleotides 1–1534 of SEQ ID NO: 3 was ligated into the remaining vector/ABCA-1 promoter fragment produced by this digestion. The resultant plasmid, pAPR1, encodes the luciferase reporter gene under transcriptional control of 1.75 kb of the human ABCA-1 promoter sequence.

Transfection of Reporter Constructs: The above-described control or pAPR1 plasmid was transfected into confluent cultures of RAW 264.7 cells maintained in DMEM containing 10% fetal bovine serum. Each well of a 12 well dish was transfected for 5 hours with either pGL3-Basic, pGL3-Promoter or pAPR1 DNA (1 µg), luciferase plasmid DNA (1 µg), and 12 µl of Geneporter reagent (Gene Therapy Systems, San Diego, Calif.; Cat. #T201007). In addition, 0.1 µg of pCMVβ plasmid DNA (Clontech, Palo Alto, Calif., Cat. #6177-1) was added as a control for transfection efficiency. After 5 hours, the culture medium was replaced with serum-free DMEM/BSA in the presence of or absence of acetylated LDL (100 µg/ml) and incubated for 24 hours.

For added convenience in high throughput screening, cultured cells can be stably transfected with reporter plasmids using the following procedure. First, 5×10⁶ RAW 264.7 cells are transfected for 5 hours in a 60 mm dish with 9 µg of the pAPR1 plasmid and pCMVscript (Stratagene, LaJolla, Calif.) in 10 ml of serum-free DMEM with 50 µl Geneporter transfection reagent (Gene Therapy Systems, San Diego, Calif.). Subsequently, the transfection medium is replaced with complete medium and the cells incubated overnight at 37° C. Subsequently, the cells are transferred to separate dishes at dilutions ranging from 1:5 to 1:1000 and incubated in selection medium containing 800 µg/ml G418 (Life Technologies, Bethesda, Md.) for 20 days. Visible colonies are picked, expanded, and assayed for luciferase activity as described below. Using this method, five clonal cell lines positive for luciferase activity were identified for use in high throughput assays.

Luciferase Assay: Following transfection, the cells in each well were lysed in 70 µl of 1X cell lysis reagent (Promega, Madison, Wis., Cat. #E3971), subjected to one freeze-thaw cycle, and the lysate cleared by centrifugation for 5 minutes at 12,000 g. After centrifugation, 100 µl of luciferase assay reagent (Promega, Madison, Wis.; Cat. #E1501) was added to 10 µl of lysate. The luciferase activity of each lysate was measured as light units using a luminometer. Additionally, the β-galactosidase activity of each lysate was measured using the chemiluminescent assay reagents supplied in the Galacto-light kit according to the manufacturer's instructions (Tropix Inc., Bedford, Mass.: Cat. #BL100G). The normalized luciferase activity for each lysate was determined by dividing the luciferase activity value by the determined β-galactosidase value and reported as relative light units.

The compounds of the invention demonstrated increased ABCA-1 gene expression in this assay.

EXAMPLE 11 mRNA ASSAYS

Modulation of expression of ABCA-1 mRNA levels by the compounds of the invention were determined in the following assays.

Quantitative PCR

Cultures of THP were grown to subconfluence in DMEM/10% FBS before replacement with DMEM/BSA and the indicated additive for 24 or 48 hours. RNA using standard methods.

Quantitative PCR was carried out using the GeneAmp 5700 Sequence Detection System (Perkin-Elmer Applied Biosystems, Foster City, Calif.). Briefly, 500 ng of DNAse-treated mRNA was reverse transcribed using random hexamer primers at 2.5 µM. Approximately 5% of this reaction was amplified by PCR using the SYBR green core kit (PE Applied Biosystems, Foster City, Calif.; Cat. #4304886) and human ABCA-1 primers LF:5'-CCTCTCATTACACAAAAACCAGAC (SEQ ID NO: 11) and LR:5'-GCTTTCTTTCACTTCTCATCCTG (SEQ ID NO: 12) to yield an 82 bp fragment corresponding to nucleotides 7018–7099 of human ABCA-1. PCR cycle conditions were as follows: 10 minutes 95° C.; followed by 40 cycles of 95° C., 15 seconds; and 60° C., 60 seconds. The mRNA in each sample was quantitated by detecting the increase in fluorescence caused by SYBR green binding to the double-stranded amplification product generated during each PCR cycle. All samples were run in triplicate and normalized against β-actin mRNA, amplified in parallel reactions with primers actin F:5'-TCACCCACACTGTGCCATCTACGA (SEQ ID NO: 54) and actin B:5'-CAGCGGAACCGCTCATTGCCAATGG (SEQ ID NO: 55). Standard curves were run for both ABCA-1 and M-actin on the same PCR plate.

Changes in mRNA levels were also determined using RAW 264.7 cells with a QuantiGene® Expression Kit from Bayer.

The compounds of the invention modulated expression of ABCA-1 mRNA levels in this assay.

EXAMPLE 12

Lipid Efflux Assay

This example demonstrates that enhanced expression of ABCA-1 protein in the plasma membrane is associated with lipid efflux.

Cell-surface labeling and immunoprecipitation is used to determine whether increased expression of ABCA-1 protein in the plasma membrane is correlated with an increase in cholesterol efflux. The relative amount of ABCA-1 on the cell surface is determined by cross-linking surface proteins on intact cells with the membrane-impermeable agent sulfo-NHS-biotin, followed by the steps of membrane solubilization, immunoprecipitation with ABCA-1 antibody, SDS-PAGE, and detection with streptavidin.

Cell Culture: Fibroblasts are cultured under control conditions and conditions known to increase cholesterol efflux (Oram, et al., J. Lip. Res., 40: 1769–1781 (1999)). Control cells are grown to confluence in DMEM/10% FBS and then incubated in DMEM/BSA for 18 hours with no additives (control). cAMP-treated cells are grown to confluence in DMEM/10% FBS and then incubated in DMEM/BSA for 18 hours with 1 mM 8-Br-cAMP(cAMP). Cholesterol-loaded cells are grown to confluence in DMEM/10% FBS and then incubated in DMEM/BSA for 48 hours with 30 µg/ml cholesterol plus 18 hours with no additives (cholesterol). Cholesterol-loaded cells treated with cAMP are grown to confluence in DMEM/10% FBS and then incubated in DMEM/BSA for 48 hours with 30 µg/ml cholesterol plus 18 hours with 1 mM 8-Br-cAMP (cholesterol+cAMP).

Cell-Surface Labeling: For selective labeling of plasma membrane ABCA-1, the cells are incubated for 30 minutes at 0° C. with PBS containing 1 mg/ml sulfo-NHS-biotin (Pierce, Rockford, Ill.; Cat. #21217) to biotinylate cell-surface proteins (see Walker et al., Biochemistry, 50:14009–14014 (1993)).

Immunoprecipitation: Rabbit antiserum for ABCA-1 is raised against a synthetic peptide corresponding to the deduced peptide KNQTVVDAVLTSFLQDEKVKES located at the C-terminus of human ABCA-1. Immunoprecipitation is performed by solubilizing the cells in PBS containing 1% Triton X-100 (Sigma, St. Louis, Mo.) and protease inhibitors leupeptin (1 mM), pepstatin (1 mM), and aprotinin (1 mM). The cell extract is incubated overnight at 4° C. with anti-ABCA-1 antiserum at 1:200 dilution followed by an additional 1 hour incubation with 5 µl proteinA-coated magnetic beads (Dynal, Lake Success, N.Y.; Cat. #1001.01). The antibody-antigen complex is sedimented with a magnet, the beads are ished twice with 1% Triton-X/PBS, and the proteins are eluted with 1% acetic acid.

Detection of ABCA-1 Protein: The eluted biotinylated proteins are subjected to SDS-PAGE (6% gel; 150V, 5 hours) and transferred to nitrocellulose membrane (200 mA, 18 hours). The nitrocellulose is probed with streptavidin-horse radish peroxidase (Amersham Pharmacia, Piscataway, N.J.; Cat. #RPN 1231) diluted 300-fold and detected by enhanced chemiluminescence labeling (ECL) according to vendor's protocol (Amersham Pharmacia, Piscataway, N.J.). To test for possible biotinylation of intracellular proteins, the post-immunoprecipitation supernatant is treated with a mouse monoclonal antibody to the intracellular protein β-COP and immunoprecipitated biotinylated 5-COP is assayed by streptavidin blotting.

EXAMPLE 13

The ability of the compounds of the invention to stimulate cholesterol efflux from cells was determined in the following assay.

RAW 264.7 cells were loaded with cholesterol as described in Smith et al., J. Biol. Chem., 271:30647–30655 (1996). Briefly, semi-confluent cells plated in 48-well dishes were incubated in 0.2 ml of DMEM supplemented with 4.5 g/L glucose, 0.1 g/L sodium pyruvate and 0.584 g/L of glutamine, 10% fetal bovine serum, 50 µg/ml acetylated low density lipoprotein (AcLDL) and 0.5 µCi/ml of [$^3$H]-cholesterol. After 18 hr, cells were washed two times with PBS containing 1% BSA and incubated overnight (16–18 hours) in DMEM/1% BSA to allow for equilibration of cholesterol pools. The cells were then rinsed four times with PBS/BSA and incubated for one hour at 37° C. with DMEM/BSA. Efflux medium (DMEM/BSA) containing either albumin alone (control), albumin plus HDL (40 µg protein/ml), or albumin plus apo A–I (20 µg/ml, Biodesign International, Kennebunk, Me.) was added and the cells were incubated for 4, 24, or 48 hours.

Cholesterol efflux was measured by removing the medium, washing the cell layer and extracting the cells. Cellular radioactivity was measured by scintillation counting after solubilization in 0.5 ml of 0.2M NaOH (Smith et al., J. Biol. Chem., 271:30647–30655 (1996)) or extraction in hexane:isopropanol (3:2 v/v) as described in Francis et al., J. Clin. Invest., 96, 78–87 (1995). The labelled phospholipid remaining in the medium was also determined by liquid scintillation counting. The efflux of cholesterol was expressed as the percentage of tritiated lipid counts in the medium over the total tritiated lipid counts recovered from the cells and medium (cpm medium cpm (medium+lysate)× 100).

Cholesterol efflux was also determined in THP cells. Replicate cultures of THP cells were plated in 48 well dishes using the method described (see Kritharides et al Thrombo Vasc Biol 18, 1589–1599,1998). Cells were plated at an initial density of 500,000 cells/well. After addition of PMA (100 ng/ml), the cultures were incubated for 48 hr at 37° C. The medium was aspirated and replaced with RPMI-1640 medium containing 2 mg/ml of FAFA, 50 µg/ml of acetylated LDL and 3 µCi/ml of radiolabeled cholesterol. After an overnight incubation, the medium was aspirated, the wells washed extensively with PBS. 0.2 ml of RPMI-1640 medium containing 2 mg/ml of FAFA was added to each well. The compound of interest was added to a final concentration of 10 µM. After 4 hr, Apolipoprotein A1 (10 µg/ml) was added to some wells and the cultures incubated for 24 hr. The medium was harvested and assayed for radioactivity. The amount of radioactivity in the cell layer was ascertained by adding 0.2 ml of 2 M NaOH and counting the lysed cells. The percent cholesterol efflux was calculated as described above.

The compounds of the invention stimulated cholesterol efflux in this assay.

EXAMPLE 14

The relationship between ABCA-1 expression and HDL levels are determined in the following in vivo assay.

Candidate compounds that increase ABCA-1 expression in vitro and are pharmacologically active and available in vivo are administered daily at a predetermined dosage to 7 week old male C57B1/6 mice either by intraperitoneal injection or by gavage in 10% Cremaphore (BASF)/saline. Three to 4 hours after the final injection, fasted EDTA-plasma and appropriate tissues are collected for analysis. Plasma HDL is isolated by phosphotungstic acid precipitation (Sigma) and HDL cholesterol, total cholesterol and triacylglycerols are determined enzymatically using kits (Roche Diagnostics). Changes to HDL cholesterol and size are further analyzed by FPLC using two Superose 6/30 columns connected in series with cholesterol in the eluted fractions detected enzymatically. In vivo changes in ABCA-1 gene expression are further confirmed by RT-PCR analysis of RNA isolated from candidate tissues.

A correlation between ABCA-1 expression and HDL levels was observed in this assay.

What is claimed is:

1. A method of treating a disease state in a mammal that is alleviable by treatment with an agent capable of increasing ABCA-1 expression, comprising administering to a mammal in need thereof a therapeutically effective dose of a compound of the Formula I:

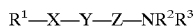 Formula I wherein:
- $R^1$ is optionally substituted alkyl, optionally substituted alkenyl, optionally substituted alkynyl, optionally substituted cycloalkyl, optionally substituted heterocyclyl, optionally substituted aryl, optionally substituted aralkyl, optionally substituted heteroaryl, or optionally substituted heteroaralkyl;
- $R^2$ and $R^3$ are independently hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl; or
- $R^2$ and $R^3$ when taken together with the nitrogen atom to which they are attached form a heterocyclic moiety;
- X is oxygen, sulfur, or —$NR^4$—;
- Y is optionally substituted alkylene or a covalent bond; wherein $R^4$ is hydrogen, optionally substituted alkyl, optionally substituted cycloalkyl, —$S(O)_2R^5$, —$C(O)R^5$, or —$C(O)NHR^5$, in which $R^5$ is optionally substituted lower alkyl, optionally substituted cycloalkyl, optionally substituted heterocyclyl, optionally substituted aryl, or optionally substituted heteroaryl; and
- Z is —$C(O)$—$Z^1$—, —$C(S)$—$Z^1$—, or —$SO_2$—$Z^1$—; in which $Z^1$ is lower alkylene or a covalent bond;

with the proviso that
  i. when $R^1$, $R^2$, or $R^3$ is alkenyl or alkynyl, the double bond of the alkenyl or the triple bond of the alkynyl is located at least two carbon atoms away from the attachment to the nitrogen;
  ii. when X is $NR^4$, Y and $Z^1$ are not both covalent bonds; and
  iii. when X is $NR^4$, $R^3$ and $R^4$ are not both hydrogen.

2. The method of claim 1, wherein Y is optionally substituted alkylene and Z is —$C(O)$—$Z^1$— or —$C(S)$—$Z^1$—, in which $Z^1$ is a covalent bond.

3. The method of claim 2, wherein X is —$NR^4$, in which $R^4$ is hydrogen, optionally substituted alkyl, optionally substituted acyl, or —$C(O)NHR^5$.

4. The method of claim 3, wherein $R^1$ and $R^2$ are optionally substituted cycloalkyl and $R^3$ is optionally substituted aryl or optionally substituted heteroaryl.

5. The method of claim 4, wherein $R^2$ is optionally substituted cyclohexyl, $R^3$ is optionally substituted phenyl, and Y is methylene.

6. The method of claim 5, wherein Z is —$C(O)$—.

7. The method of claim 6, wherein $R^4$ is hydrogen.

8. The method of claim 7, wherein $R^1$ is (2S, 1R,4R) bicyclo[2.2.1]hept--2-yl, $R^2$ is cyclohexyl and $R^3$ is phenyl, namely 2-[(2S,1R,4R)bicyclo[2.2.1]hept-2-ylamino)-N-cyclohexyl-N-phenylacetamide.

9. The method of claim 7, wherein $R^1$ is 1-adamantyl, $R^2$ is cyclohexyl and $R^3$ is phenyl, namely 2-(adamant-1-ylamino)-N-cyclohexyl-N-phenylacetamide.

10. The method of claim 7, wherein $R^1$ is 1,3,3-trimethylbicyclo[2.2.1-]hept-2-yl, $R^2$ is cyclohexyl and $R^3$ is phenyl, namely 2-(1,3,3-trimethylbicyclo[2.2.1]hept-2-ylamino)-N-cyclohexyl-N-phenylacetamide.

11. The method of claim 7, wherein $R^1$ is (1S,3S,4S)-3,5,5-trimethylbi-cyclo [2.2.1]hept-2-yl, $R^2$ is cyclohexyl and $R^3$ is phenyl, namely 2-[((1S,3S,4S)-3,5,5-trimethylbicyclo[2.2.1]hept-2-yl)amino]-N-cyclohexyl-N-phenylacetamide.

12. The method of claim 7, wherein $R^1$ is 7,7-dimethylbicyclo[2.2.1]he-pt-2-yl, $R^2$ is cyclohexyl and $R^3$ is phenyl, namely 2-[(7,7-dimethylbicyclo[2.2.1]hept-2-yl)amino]-N-cyclohexyl-N-phenylacetamide.

13. The method of claim 7, wherein $R^1$ is (1R,2R)-2-methylcyclohexyl, $R^2$ is cyclohexyl and $R^3$ is phenyl, namely 2-[(1R,2R)-2-methylcyclohexylamino]-N-cyclohexyl-N-phenylacetamide.

14. The method of claim 7, wherein $R^1$ is (5S,2R)-5-methyl-2-isopropyl-cyclohexyl, $R^2$ is cyclohexyl and $R^3$ is phenyl, namely 2-[(5S,2R)-5-methyl-2-isopropylcyclohexylamino]-N-cyclohexyl-N-phenylacetamide.

15. The method of claim 6, wherein $R^4$ is —$C(X^1)NHR^5$.

16. The method of claim 15, wherein $R^5$ is lower alkyl.

17. The method of claim 16, wherein $R^1$ is 1,3,3-trimethylbicyclo[2.2.-1]hept-2-yl, $R^2$ is cyclohexyl, $R^3$ is phenyl, and $R^4$ is —C(O)NHR5 in which $R^5$ is methyl, namely 2-[(methylamino)-N-(1,3,3-trimethylbicyclo[2.2.1]hept-2-yl)carbonylamino]—N-cyclohexyl-N-phenylacetamide.

18. The method of claim 16, wherein $R^1$ is 1,3,3-trimethylbicyclo[2.2.1]hept-2-yl, $R^2$ is cyclohexyl, $R^3$ is phenyl, and R⁴ is —C(S)NHR5 in which R⁵ is methyl, namely 2-[(methylamino)-N-(1,3,3-trimethylbicyclo[2.2.1]hept-2-yl)thiocarbonylamino]-N-cyclohexyl-N-phenylacetamide.

19. The method of claim 5, wherein Z is —C(S)—.

20. The method of claim 19, wherein R⁴ is hydrogen.

21. The method of claim 20, wherein R¹ is 1,3,3-trimethylbicyclo[2.2.-1]hept-2-yl, R² is cyclohexyl and R³ is phenyl, namely 2-[(1,3,3-trimethylbicyclo[2.2.1]hept-2-yl)amino]-N-cyclohexyl-N-phenylthioacetamide.

22. The method of claim 1, wherein Z is —C(O)—Z¹— or —C(S)—Z¹—, in which Z¹ is lower alkylene.

23. The method of claim 22, wherein and X is —NR⁴, in which R⁴ is hydrogen, optionally substituted alkyl, —C(O)R⁵, or —C(O)NHR⁵.

24. The method of claim 23, wherein R¹ and R² are optionally substituted cycloalkyl and R³ is optionally substituted aryl or optionally substituted heteroaryl.

25. The method of claim 24, wherein R² is optionally substituted cyclohexyl, R³ is optionally substituted phenyl, and Y is methylene.

26. The method of claim 25, wherein Z is —C(O)—, and R⁴ is hydrogen.

27. The method of claim 26, wherein R¹ is 1,3,3-trimethylbicyclo[2.2.-1]hept-2-yl, R² is cyclohexyl and R³ is phenyl, namely 2-(cyclohexylphenylamino)-N-(1,3,3-trimethylbicyclo[2.2.1]hept-2-yl)acetamide.

28. A method for treating a disease or condition in a mammal that can be usefully treated with a compound that elevates serum levels of HDL cholesterol, comprising administering to a mammal in need thereof a therapeutically effective dose of a compound of claim 1.

29. The method of claim 28, wherein the disease state or condition is coronary artery disease or atherosclerosis.

30. A method for treating a disease or condition in a mammal related to low HDL cholesterol levels, comprising administering to a mammal in need thereof a therapeutically effective dose of a compound of claim 1.

31. The method of claim 30, wherein the disease state or condition is coronary artery disease or atherosclerosis.

32. A method for treating a disease or condition in a mammal that can be usefully treated with a compound that promotes cholesterol efflux from cells, comprising administering to a mammal in need thereof a therapeutically effective dose of a compound of claim 1.

33. The method of claim 32, wherein the disease state or condition is coronary artery disease or atherosclerosis.

34. A method for treating a condition related to coronary artery disease in a mammal that can be usefully treated with a combination of a compound that elevates serum levels of HDL cholesterol and a compound that lowers LDL cholesterol, comprising administering to a mammal in need thereof a therapeutically effective dose of a compound of claim 1 and a compound that lowers LDL cholesterol.

35. The method of claim 34, wherein the LDL cholesterol lowering compound is chosen from clofibrate, gemfibrozil, and fenofibrate, nicotinic acid, mevinolin, mevastatin, pravastatin, simvastatin, fluvastatin, lovastatin, cholestyrine, colestipol and probucol.

36. A compound of the Formula I:

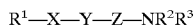    R¹—X—Y—Z—NR²R³    Formula I wherein:
R¹ is optionally substituted alkyl, optionally substituted alkenyl, optionally substituted alkynyl, optionally substituted cycloalkyl, optionally substituted heterocyclyl, optionally substituted aryl, optionally substituted aralkyl, optionally substituted heteroaryl, or optionally substituted heteroaralkyl;

R² is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

R³ is optionally substituted phenyl; or

R² and R³ when taken together with the nitrogen atom to which they are attached form a heterocyclic moiety;

X is oxygen, sulfur, or —NR⁴—;

Y is optionally substituted alkylene or a covalent bond; wherein R4 is hydrogen, optionally substituted alkyl, optionally substituted cycloalkyl, —S(O)₂R⁵,—C(O)R⁵, or —C(O)NHR⁵, in which R⁵ is optionally substituted lower alkyl, optionally substituted cycloalkyl, optionally substituted heterocyclyl, optionally substituted aryl, or optionally substituted heteroaryl; and Z is —C(O)—Z¹—, —C(S)—Z¹—, or —S₂—Z¹—; in which Z¹ is lower alkylene or a covalent with bond;

the proviso that
i. when R¹, or R² is alkenyl or alkynyl, the double bond of the alkenyl or the triple bond of the alkynyl is located at least two carbon atoms away from the attachment to the nitrogen; and
ii. when R² is hydrogen, R³ is phenyl, x is —NR⁴, Y is a covalent bond, and Z is —C(S)—CH₂—, then R¹ cannot be phenyl optionally substituted by methyl or halo;
iii. when R² is hydrogen, R³ is phenyl, X is —NR⁴, Y is methylene, and Z is —C(S)—, then R⁴ cannot be methyl or ethyl when R¹ is cyclohexyl; and
iv when X is NR⁴, R³ and R⁴ are not both hydrogen.

37. The compound of claim 36, wherein Y is optionally substituted alkylene and Z is —C(O)—Z¹— or —C(S)—Z¹—, in which Z¹ is a covalent bond.

38. The compound of claim 37, wherein X is —NR⁴, in which R⁴ is hydrogen, optionally substituted alkyl, optionally substituted acyl, or —C(O)NHR⁵.

39. The compound of claim 38, wherein R¹ and R² are optionally substituted cycloalkyl.

40. The compound of claim 39, wherein R² is optionally substituted cyclohexyl, and Y is methylene.

41. The compound of claim 40, wherein Z is —C(O)—.

42. The compound of claim 41, wherein R⁴ is hydrogen.

43. The compound of claim 42, wherein R¹ is (2S,1R,4R)bicyclo[2.2.1]h- ept-2-yl, R² is cyclohexyl and R³ is phenyl, namely 2-[(2S,1R,4R)bicyclo[2.2.1]hept-2-ylamino)-N-cyclohexyl-N-phenylacetamide-.

44. The compound of claim 42, wherein R¹ is 1-adamantyl, R² is cyclohexyl and R³ is phenyl, namely 2-(adamant-1-ylamino)-N-cyclohexyl-N-phenylacetamide.

45. The compound of claim 42, wherein R¹ is 1,3,3-trimethylbicyclo[2.2.1]hept-2-yl, R² is cyclohexyl and R³ is phenyl, namely 2-(1,3,3-trimethylbicyclo[2.2.1]hept-2-ylamino)-N-cyclohexyl-N-phenylacetamide.

46. The compound of claim 42, wherein R¹ is (1S,3S,4S)-3,5,5-trimethylbicyclo [2.2.1]hept-2-yl, R² is cyclohexyl and R³ is phenyl, namely 2-[((1S,3S,4S)-3,5,5-trimethylbicyclo[2.2.1]hept-2-yl)amino]-N-cyclohexyl-N-phenylacetamide.

47. The compound of claim 42, wherein R¹ is 7,7-dimethylbicyclo[2.2.1]hept-2-yl, R² is cyclohexyl and R³ is phenyl, namely 2-[(7,7-dimethylbicyclo[2.2.1]hept-2-yl)amino]-N-cyclohexyl-N-phenylacetamide.

48. The compound of claim 42, wherein R¹ is (1R,2R)-2-methylcyclohexyl, R² is cyclohexyl and R³ is phenyl, namely 2-[(1R,2R)-2-methylcyclohexylamino]-N-cyclohexyl-N-phenylacetamide.

49. The compound of claim 42, wherein $R^1$ is (5S,2R)-5-methyl-2-isopropylcyclohexyl, $R^2$ is cyclohexyl and $R^3$ is phenyl, namely 2-[(5S,2R)-5-methyl-2-isopropylcyclohexylamino]-N-cyclohexyl-N-phenylacetamide.

50. The compound of claim 41, wherein $R^4$ is —C($X^1$)NHR$^5$.

51. The compound of claim 50, wherein $R^5$ is lower alkyl.

52. The compound of claim 51, wherein $R^1$ is 1,3,3-trimethylbicyclo[2.2.1]hept-2-yl, $R^2$ is cyclohexyl, $R^3$ is phenyl, and $R^4$ is —C(O)NHR$^5$ in which $R^5$ is methyl, namely 2-[(methylamino)-N-(1,3,3-trimethylbicyclo[2.2.1]hept-2-yl)carbonylamino]-N-cyclohexyl-N-phenylacetamide.

53. The compound of claim 51, wherein $R^1$ is 1,3,3-trimethylbicyclo[2.2.1]hept-2-yl, $R^2$ is cyclohexyl, $R^3$ is phenyl, and $R^4$ is —C(S)NHR$^5$ in which $R^5$ is methyl, namely 2-[(methylamino)-N-(1,3,3-trimethylbicyclo[2.2.1]hept-2-yl)thiocarbonylamino]-N-cyclohexyl-N-phenylacetamide.

54. The compound of claim 40, wherein Z is —C(S)—.

55. The compound of claim 54, wherein $R^4$ is hydrogen.

56. The compound of claim 55, wherein $R^1$ is 1,3,3-trimethylbicyclo[2.2.1]hept-2-yl, $R^2$ is cyclohexyl and $R^3$ is phenyl, namely 2-[(1,3,3-trimethylbicyclo[2.2.1]hept-2-yl)amino]-N-cyclohexyl-N-phenylthioacetamide.

57. The compound of claim 36, wherein Z is —C(O)—$Z^1$— or —C(S)—$Z^1$—, in which $Z^1$ is lower alkylene.

58. The compound of claim 57, wherein X is —NR$^4$, in which $R^4$ is hydrogen, optionally substituted alkyl, —C(O)R$^5$, or —C(O)NHR$^5$.

59. The compound of claim 58, wherein $R^1$ and $R^2$ are optionally substituted cycloalkyl and $R^3$ is optionally substituted phenyl.

60. The compound of claim 59, wherein $R^2$ is optionally substituted cyclohexyl and Y is methylene.

61. The compound of claim 60, wherein Z is —C(O)—, and $R^4$ is hydrogen.

62. The compound of claim 61, wherein $R^1$ is 1,3,3-trimethylbicyclo[2.2.1]hept-2-yl, $R^2$ is cyclohexyl and $R^3$ is phenyl, namely 2-(cyclohexylphenylamino)-N-(1,3,3-trimethylbicyclo[2.2.1]hept-2-yl)acetamide.

63. A pharmaceutical composition comprising at least one pharmaceutically acceptable excipient and a therapeutically effective amount of a compound of claim 1.

64. A pharmaceutical composition comprising at least one pharmaceutically acceptable excipient and a therapeutically effective amount of a compound of claim 36.

* * * * *